United States Patent [19]

Bruegger

[11] Patent Number: 4,980,058

[45] Date of Patent: Dec. 25, 1990

[54] SEPARATION OF HEMOGLOBIN $A_2$ FROM HEMOGLOBIN MIXTURE

[75] Inventor: Berndt B. Bruegger, San Francisco, Calif.

[73] Assignee: Bio-Rad Laboratories, Inc., Hercules, Calif.

[21] Appl. No.: 286,432

[22] Filed: Dec. 19, 1988

Related U.S. Application Data

[62] Division of Ser. No. 118,491, Nov. 6, 1987, Pat. No. 4,810,391.

[51] Int. Cl.$^5$ .............................................. B01D 15/08
[52] U.S. Cl. ................................ 210/198.2; 210/139; 210/143; 73/61.1 C; 422/70
[58] Field of Search ............... 530/385, 413, 416, 417; 422/70; 436/66, 161; 210/635, 656, 659, 198.2, 143, 138, 139; 73/61.1 C

[56] References Cited

U.S. PATENT DOCUMENTS

| | | | |
|---|---|---|---|
| 4,108,603 | 8/1978 | Regnier | 210/656 |
| 4,159,895 | 7/1979 | Sline | 436/66 |
| 4,209,372 | 6/1980 | Bluestein | 436/66 |
| 4,209,373 | 6/1980 | Bluestein | 436/66 |
| 4,448,888 | 5/1984 | Bleile | 436/66 |
| 4,502,786 | 3/1985 | Golias | 356/40 |
| 4,604,350 | 8/1986 | DeMatteis | 436/66 |
| 4,764,279 | 8/1988 | Tayot | 436/66 |

FOREIGN PATENT DOCUMENTS

| | | | |
|---|---|---|---|
| 183181 | 6/1986 | European Pat. Off. | 436/66 |
| 56-98658 | 8/1981 | Japan | 436/66 |
| 58-72055 | 4/1983 | Japan | 436/66 |

OTHER PUBLICATIONS

DIAMAT Fully Automated Glycosylated Hemoglobin Analyzer System, Instruction Manual, Nov. 1985.

*Primary Examiner*—Ernest G. Therkorn
*Attorney, Agent, or Firm*—Townsend and Townsend

[57] ABSTRACT

An ion exchange method for the separation of hemoglobin $A_2$ from other hemoglobin components normally present in human blood involves the use of three buffer solutions in succession, with specified ionic strengths and pHs. The first has a phosphate buffer at 1 to 20 mM and a pH of 6.5 to 6.9; the second has phosphate buffer at 15 to 55 mM and a pH of 6.4 to 6.8; and the third has phosphate buffer at 60 to 100 mM and a pH of about 6.4 to 6.8. The first is continued until substantially all hemoglobin $A_{1a}$ and $A_{1b}$ has eluted from the column, the second until substantially all $A_{1c}$, F, and $A_0$ is eluted, and the third for the elution of $A_2$.

16 Claims, No Drawings

SEPARATION OF HEMOGLOBIN A₂ FROM HEMOGLOBIN MIXTURE

This is a division of application Ser. No. 07/118,491, filed Nov. 6, 1987, now U.S. Pat. No. 4,810,391.

This invention relates to chromatographic processes for hemoglobin analyses, and particularly analyses for the quantitation of hemoglobin $A_2$.

BACKGROUND AND SUMMARY OF THE INVENTION

The hemoglobin content of adult human blood contains as its major component hemoglobin A (HbA or $HbA_1$) The minor components are hemoglobin F (HbF) and hemoglobin $A_2$ ($HbA_2$) In normal subjects, the level of hemoglobin $A_2$ ranges from 1.4% to 3.2%. The hemoglobin $A_2$ level is elevated however in beta-thalassemia cases, where it frequently exceeds 3.5%. Accordingly, the determination of an elevated $HbA_2$ level is the most practical means for the diagnosis of carriers for the beta-thalassemia gene.

Methods used in clinical laboratories for the quantitation of $HbA_2$ include electrophoresis and anion-exchange microchromatography. High performance liquid chromatography (HPLC) using cation exchange resins is used by research laboratories for other hemoglobin separations, but is generally not useful for $HbA_2$ quantitation since it generally combines the $HbA_0$ and $HbA_2$ components under a single peak. The $HbA_0$ is normally present in far greater amounts than the $HbA_2$, totally obscuring any variations in the $HbA_2$ level.

For example, hemoglobin $A_{1c}$, the best defined of the hemoglobin A subfractions (collectively known as glycohemoglobins), is widely used as an indicator of diabetes mellitus Accordingly, a variety of clinical systems and products involving cation exchange have been developed for $HbA_{1c}$ quantitation. One example is the DIAMAT ™ analyzer manufactured by Bio-Rad Laboratories. Inc., Richmond, Calif., (assignee herein), a fully automated glycosylated hemoglobin analyzer system. This system pumps a sequence of elution buffers of different ionic strengths in succession through a cation-exchange HPLC column. As a result, the sample components $HbA_{1a}$, $HbA_{1b}$, HbF, and $HbA_{1c}$ emerge from the column as individual peaks, whereas the final peak contains both $HbA_0$ and $HbA_2$.

A novel cation exchange HPLC method, together with an automated system incorporating the method, has now been developed which will separate $HbA_2$ from HbA and thereby permits quantitation of $HbA_2$. The separation is achieved using lower ionic strengths for each of the three elution buffers, and longer periods of time between switching from one buffer to the next. In addition, pHs of the buffer solutions are somewhat higher. Thus, by simple substitution of buffer solutions and readjustment of switching times, instrumentation designed for quantitation of $HbA_1$ fractions is readily converted to one useful for the quantitation of $HbA_2$.

DETAILED DESCRIPTION OF THE INVENTION AND PREFERRED EMBODIMENTS

Separation media to which the present invention are directed are weak cation exchange media, and preferably those used in high performance liquid chromatography. Examples are naturally occurring resins as well as synthetic resins, including those with carboxylic acid, phenolic and phosphonic functional groups. Carboxylic acid functional groups are preferred.

The cation exchanger is preferably supported on an inert base, enhancing the contact area of the cation exchanger. Gel particles are one example, with those having average pore diameters Within the range of about 100 to about 150 Angstroms particularly preferred.

In accordance with the invention, three buffer solutions are used in sequence. The first contains a phosphate buffer at a concentration of from about 1 to about 20 mM and a pH of from about 6.5 to about 6.9. The second contains phosphate buffer at a concentration of from about 15 to about 55 mM, a pH of about 6.4 to about 6.8. The third contains phosphate buffer concentration of from about 60 to about 100 mM and a pH of from about 6.4 to about 6.8. In preferred embodiments, the phosphate buffer concentrations and pHs are as follows: buffer No. 1—about 5 to about 15 mM phosphate, pH about 6.6 to about 6.8; buffer No. 2—about 25 to about 45 mM phosphate, pH from about 6.5 to about 6.7; buffer No. 3—about 70 to about 90 mM phosphate, pH from about 6.5 to about 6.7.

In further preferred embodiments, bis-tris buffer is included in the buffer solutions as well. "Bis-tris" is a commonly used abbreviation for 2.2-bis(hydroxymethyl)-2,2',2"-nitrilotriethanol. The following concentrations of bis-tris will provide the best bis(hydro results: first buffer solution—about 30 to about 50 mM, preferably about 35 to about 45 mM: second buffer solution—about 20 to about 60 mM. preferably about 30 to about 50 mM; third buffer solution—about 20 to about 60 mM. preferably about 30 to about 50 mM.

The volume of each buffer solution, i.e., the length of time during which any particular buffer solution will be pumped through the column, will be selected such that the following elutions occur: the first buffer solution will be passed through the column in sufficient quantity to elute substantially all hemoglobin $A_{1a}$ and $A_{1b}$ from the column: the second buffer solution will then be passed in sufficient quantity to cause the elution of substantially all of the hemoglobin $A_{1c}$, F and $A_0$; and the third buffer solution will then be passed in sufficient quantity to elute substantially all of the hemoglobin $A_2$. The actual amounts will of course vary depending on the column diameter, and possibly sample size as well. In general, appropriate amounts of the first buffer solution will range from about 5 mL to about 10 mL per square centimeter of column cross section. Likewise, appropriate amounts of the second buffer solution will range from about 45 mL to about 55 mL per square centimeter of column cross section, and appropriate amounts of the third buffer solution will range from about 40 mL to about 50 mL per square centimeter of column cross section.

In further preferred embodiments, the buffer solutions contain from about 0.01% to about 1.0% sodium azide, preferably from about 0.03% to about 0.3%.

The cation exchanger may assume a variety of configurations. An elongate column such as those generally used in HPLC apparatus is preferred. A typical column will range from about 1 mm to about 10 mm in internal diameter, and from about 5 to about 50 cm. preferably from about 10 cm to about 25 cm. in length. The pressure drop across the column will vary depending on the column length and diameter and the density or particle size of the ion exchanger. Best results will generally be obtained at pressure drops ranging from about 10 to about 100 psig.

Such a column is preferably operated at approximately ambient temperature. The flow rates of the buffer solutions through the column may also vary widely, although best results will generally be obtained at flow rates ranging from about 1 mL to about 30 mL per minute, and preferably from about 5 to about 10 mL per minute, per square centimeter of column cross section.

The sample size used for analysis will also vary widely depending on the column geometry. One advantage of the system of the present invention, however, is that it permits the use of very small sample sizes providing fast analyses. Preferred sample sizes range from about 1 microliter to about 100 microliters.

Automated systems may be used to carry out the method described above. Any automated HPLC apparatus having connections for at least three buffer solutions and a timing mechanism for switching among the three solutions can be used. The DIAMAT TM system referred to above is one example.

The following examples are offered primarily for purposes of illustration, and are intended neither to define nor limit the invention in any manner.

EXAMPLES

An existing instrument designed for the quantitation of hemoglobin $A_{1c}$ was modified in accordance with the present invention. The instrument was the DIAMAT TM Model 723 Fully Automated Glycosylated Hemoglobin Analyzer System, a product of Bio-Rad Laboratories. Inc., Hercules, Calif. The instrument is a cation-exchange HPLC system, which contains a single piston pump with a step-gradient valve system allowing three phosphate buffers of increasing ionic strength to pass through the analytical column in a combined sequence. The analytical column is 4 mm I.D. × 15 cm and contains spherical cation exchange gel consisting of a carboxymethyl functional group on a silica base with particle size 6.5 microns. A particle size range contemplated for use with this instrument is 4 to 7 microns. During operation, the column is maintained at a temperature of 23° C. The system uses a visible wavelength detector at 415 nm and 690 nm and a thermal printer. It automatically injects samples of preselected volume, and maintains a buffer flow rate of 1 mL/min (8 mL/min per square centimeter of column cross section) ±0.3% through the column. The instrument contains reservoirs for the three buffer solutions and a wash solution, with an automatic timed switching mechanism which draws liquid from the reservoirs in succession for specified time periods for pumping through the column. The instrument is designed for $HbA_{1c}$ determination, and the solutions supplied with it for this purpose are as follows:

TABLE 1

| SOLUTIONS FOR $HbA_{1c}$ DETERMINATION | | | | |
|---|---|---|---|---|
| | Buffer #1 | Buffer #2 | Buffer #3 | Wash Solution |
| sodium phosphate | 74 mM | 120 mM | 250 mM | 2.7 mM |
| sodium azide | 0.1% | 0.1% | 0.1% | 0.1% |
| pH | 5.8 | 5.7 | 5.6 | 6.4 |

All solutions are aqueous solutions.

The timing sequence is likewise designed for $HbA_{1c}$ separation, and is accordingly set as follows: Buffer #1 is pumped through the column for the first 1.7 minutes after sample injection, followed by Buffer #2 for 2 minutes, followed by Buffer #3 for 2.1 minutes, followed by Buffer #1 again for 2.2 minutes. The resulting volumes of buffer solution, expressed in mL per square centimeter of column cross section, are 13.5 for Buffer #1 (first portion). 15.9 for Buffer #2, 16.7 for Buffer #3, and 17.5 for Buffer #1 (final portion). Hemoglobin components emerge from the column in the following order, $A_{1a}$, $A_{1b}$F, and $A_{1c}$ in individual peaks, followed by a single peak containing both $A_0$ and $A_2$.

To modify the system in accordance with the present invention, the buffer and wash solutions were replaced by the following:

TABLE 2

| SOLUTIONS FOR $HbA_2$ DETERMINATION | | | | |
|---|---|---|---|---|
| | Buffer #1 | Buffer #2 | Buffer #3 | Wash Solution |
| bis-Tris | 0.04M | 0.04M | 0.04M | 0.004M |
| Sodium phosphate | 0.010M | 0.036M | 0.080M | 0.0 |
| Sodium azide | 0.012M | 0.012M | 0.012M | 0.012M |
| Potassium cyanide | 0.003M | 0.003M | 0.003M | 0.0 |
| pH | 6.7 | 6.6 | 6.6 | 6.7 |

The term "bis-tris" is used here according to its common meaning, i.e., as an abbreviation for 2,2-bis(hydroxymethyl)-2,2', 2''-nitrilotriethanol. The sodium phosphate in Buffers #1 and #2 was sodium phosphate monobasic, while a combination of monobasic and dibasic at a weight ratio of 8:3 was used in Buffer #3. The pH was adjusted with phosphoric acid, and as before, all solutions were aqueous solutions. In addition, the timing cycle was adjusted as follows: Buffer #1 to be pumped through for 1.0 minute after sample injection, followed by Buffer #2 for 6.4 minutes, followed by Buffer #3 for 5.6 minutes, followed by Buffer #1 again for 3.0 minutes. The resulting volumes, expressed in mL per square centimeter of column cross section, are 7.9 for Buffer #1 (first portion). 50.9 for Buffer #2, 44.6 for Buffer #3, and 23.9 for Buffer #4 (final portion).

Blood samples from normal human subjects were analyzed on the instrument using both arrangements. In the tables which follow, each entry represents a single peak. The "peak area" figure is the output of an electronic integrator, and the retention time is expressed in minutes from the sample injection. Sample sizes were 20 microliters.

TABLE 3

| ANALYSIS USING $HbA_{1c}$ ARRANGEMENT | | | |
|---|---|---|---|
| Species | Retention Time | Peak Area | Percent |
| $A_{1a}$ | 1.8 | 9.17 | 0.2 |
| $A_{1b}$ | 2.4 | 72.49 | 1.8 |
| F | 3.0 | 41.83 | 1.0 |
| $A_{1c}$ | 4.4 | 502.92 | 12.4 |
| $A_0 + A_2$ | 6.0 | 3422.12 | 84.5 |

As indicated in the last entry of Table 3, the $HbA_0$ and $HbA_2$ emerged as a single peak.

TABLE 4

| ANALYSIS USING NEW ARRANGEMENT FOR $HbA_2$ | | | |
|---|---|---|---|
| Species | Retention Time | Peak Area | Percent |
| Sample No. 1: | | | |
| $A_{1a}$ | 1.6 | 121.88 | 1.6 |
| $A_{1b}$ | 2.3 | 68.78 | 0.9 |
| $A_{1c}$ | 3.4 | 376.93 | 5.0 |

TABLE 4-continued
ANALYSIS USING NEW ARRANGEMENT FOR HbA$_2$

| Species | Retention Time | Peak Area | Percent |
|---|---|---|---|
| Peak 4* | 6.4 | 8.92 | 0.1 |
| A$_0$ | 7.4 | 6785.83 | 89.9 |
| A$_2$ | 9.8 | 132.66 | 1.7 |
| Peak 7* | 11.6 | 53.17 | 0.7 |
| Peak 8* | 15.3 | 3.28 | 0.0 |
| Sample No. 2: | | | |
| A$_{1a}$ + A$_{1b}$ | 1.6 | 201.73 | 2.7 |
| A$_{1c}$ | 3.4 | 300.15 | 4.1 |
| Peak 3* | 6.4 | 8.31 | 0.1 |
| A$_0$ | 7.4 | 6557.17 | 89.9 |
| A$_2$ | 9.8 | 248.32 | 3.3 |
| Peak 6* | 11.6 | 46.88 | 0.6 |
| Sample No. 3: | | | |
| A$_{1a}$ + A$_{1b}$ | 1.6 | 205.98 | 3.0 |
| A$_{1c}$ | 3.4 | 302.01 | 4.4 |
| Peak 3* | 6.4 | 7.26 | 0.1 |
| A$_0$ | 7.4 | 6003.25 | 87.0 |
| A$_2$ | 9.8 | 282.82 | 4.1 |
| Peak 6* | 11.6 | 96.38 | 1.4 |
| Peak 7* | 15.3 | 2.47 | 0.0 |

*Numbered peaks represent unidentified species.

This data demonstrates that the new buffer solutions and timing sequence produces a detectable separation of hemoglobin A$_2$ which is not achievable with the existing hemoglobin arrangement.

The foregoing is offered primarily for purposes of illustration. It will be readily apparent to those skilled in the art that one may introduce variations and modifications in the various materials and procedures described above without departing from the spirit and scope of the invention.

What is claimed is:

1. Automated apparatus for the determination of the hemoglobin A$_2$ content of a hemoglobin mixture containing hemoglobin A$_2$, said apparatus comprising:
   a column packed with a weak cation exchanger, said column having an inlet end and an outlet end;
   a first vessel containing a first buffer solution containing phosphate buffer at a concentration of from about 1 to about 20 mM and a pH of from about 6.5 to about 6.9;
   a second vessel containing a second buffer solution containing phosphate buffer at a concentration of from about 15 to about 55 mM and a pH of from about 6.4 to about 6.8;
   a third vessel containing a third buffer solution containing phosphate buffer at a concentration of from about 60 to about 100 mM and a pH of from about 6.4 to about 6.8;
   means for injecting a sample of said hemoglobin mixture into said column at said inlet end;
   means for passing liquid through said column from said inlet end to said outlet end at a steady flow rate, from said first, second and third vessels individually in accordance with a timed sequence preselected to elute from said column any hemoglobin A$_{1a}$ and A$_{1b}$ therein with said first buffer solution, then to elute any hemoglobin A$_{1c}$, F, and A$_0$ therein A$_{1c}$, F, and A$_0$ with said second buffer solution, and then to elute said hemoglobin A$_2$ with said third buffer solution; and
   means for detecting said hemoglobin A$_2$ as it emerges from said outlet end of said column.

2. Automated apparatus in accordance with claim 1 in which the concentration of said phosphate buffer in said first buffer solution is from about 5 to about 15 mM.

3. Automated apparatus in accordance with claim 1 in which the concentration of said phosphate buffer in said second buffer solution is from about 25 to about 45 mM.

4. Automated apparatus in accordance with claim 1 in which the concentration of said phosphate buffer in said third buffer solution is from about 70 to about 90 mM.

5. Automated apparatus in accordance with claim 1 in which the concentrations of said phosphate buffer in said first, second and third solutions is from about 5 to about 15 mM, from about 25 to about 45 mM, and from about 70 to about 90 mM, respectively.

6. Automated apparatus in accordance with claim 1 in which the concentrations of said phosphate buffer in said first, second and third solutions is from about 5 to about 15 mM, from about 25 to about 45 mM, and from about 70 to about 90 mM, respectively, and the pH's of said first, second and third buffer solutions are from about 6.6 to about 6.8, from about 6.5 to about 6.7, and from about 6 5 to about 6.7, respectively.

7. Automated apparatus in accordance with claim 1 in which said first, second and third buffer solutions further contain bis-tris buffer at concentrations of from about 30 to about 50 mM, from about 20 to about 60 mM, and about 20 to about 60 mM, respectively.

8. Automated apparatus in accordance with claim 1 in which said first, second and third buffer solutions further, contain bis-tris buffer at concentrations of from about 35 to about 45 mM, from about 30 to about 50 mM, and from about 30 to about 50 mM, respectively.

9. Automated apparatus in accordance with claim 1 in which said timed sequence is preselected to pass from about 5 mL to about 10 mL of said first buffer solution through said column per square centimeter of cross section of said column.

10. Automated apparatus in accordance with claim 1 in which said timed sequence is preselected to pass from about 45 mL to about 55 mL of said second buffer solution through said column per square centimeter of cross section of said column.

11. Automated apparatus in accordance with claim 1 in which said timed sequence is preselected to pass from about 40 mL to about 50 mL of said third buffer solution through said column per square centimeter of cross section of said column.

12. Automated apparatus in accordance with claim 1 in which said timed sequence is preselected to pass from about 5 mL to about 10 mL of said first buffer solution, from about 45 mL to about 55 mL of said second buffer solution, and from about 40 mL to about 50 mL of said third buffer solution through said column per square centimeter of cross section of said column.

13. Automated apparatus in accordance with claim 1 in which first, second and third buffer solutions further contain from about 0.01% to about 1.0% sodium azide.

14. Automated apparatus in accordance with claim 1 in which said column is from about 5 cm to about 50 cm in length.

15. Automated apparatus in accordance with claim 1 in which said column is from about 10 cm to about 25 cm in length.

16. Automated apparatus for the determination of the hemoglobin A$_2$ content of a hemoglobin mixture containing hemoglobin A$_2$, said apparatus comprising:

a column packed with a weak cation exchanger, said column being from about 10 cm to about 25 cm in length and having an inlet end and an outlet end;

a first vessel containing a first solution containing phosphate buffer at a concentration of from about 5 to about 15 mM and a pH of from about 6.6 to about 6.8;

a second vessel containing a second buffer solution containing phosphate buffer at a concentration of from about 25 to about 45 mM and a pH of from abort 6.5 to about 6.7;

a third vessel containing a third buffer solution containing phosphate buffer at a concentration of from about 70 to about 90 mM and a pH of from about 6.5 to about 6.7;

means for injecting a sample of said hemoglobin mixture into said column at said inlet end;

means for passing liquid through said column from said inlet end to said outlet end at a steady flow rate, from said first, second and third vessels individually in accordance with a timed sequence preselected to pass from about 5 mL to about 10 mL of said first buffer solution, then from about 45 mL to about 55 mL of said second buffer solution, and then from about 40 mL to about 50 mL of said third buffer solution through said column per square centimeter of cross section of said column; and means for detecting said hemoglobin $A_2$ as it emerges from said outlet end of said column.

* * * * *